United States Patent [19]
Cripe

[11] Patent Number: 5,207,682
[45] Date of Patent: May 4, 1993

[54] ADJUSTABLE DRILL GUIDE

[76] Inventor: Philip H. Cripe, 1112 Brubaker St., Warsaw, Ind. 46580

[21] Appl. No.: 830,589

[22] Filed: Feb. 4, 1992

[51] Int. Cl.⁵ ............................................. A61F 2/32
[52] U.S. Cl. ...................................... 606/96; 606/98
[58] Field of Search ................................... 606/96–98, 606/102

[56] References Cited

U.S. PATENT DOCUMENTS

| | | | |
|---|---|---|---|
| 3,782,373 | 1/1974 | Smythe | 128/92 |
| 3,814,089 | 6/1974 | Deyerle | 128/92 |
| 4,281,649 | 8/1981 | Derweduwen | 606/98 X |
| 4,541,424 | 9/1985 | Gross et al. | 606/98 |
| 4,622,959 | 11/1986 | Marcus | 128/92 |
| 4,667,664 | 5/1987 | Taylor et al. | 128/92 |
| 4,813,962 | 3/1989 | Deckner et al. | 623/23 |
| 4,848,327 | 7/1989 | Perdue | 128/92 |
| 4,865,025 | 9/1989 | Buzzi et al. | 128/92 |
| 4,881,535 | 11/1989 | Sohngen | 606/98 |
| 4,969,889 | 11/1990 | Greig | 606/97 |
| 4,978,351 | 12/1990 | Rozas | 606/98 |

FOREIGN PATENT DOCUMENTS

| | | | |
|---|---|---|---|
| 992045 | 1/1983 | U.S.S.R. | 606/98 |

*Primary Examiner*—Robert A. Hafer
*Assistant Examiner*—Michael Brown
*Attorney, Agent, or Firm*—Baker & Daniels

[57] ABSTRACT

An adjustable drill guide for use with an orthopaedic implant having sleeves which are adjustable to accommodate misalignment of the sleeves relative to the bores within a prosthetic implant. Each sleeve is press fitted within a retaining ring. The retaining rings are carried within a longitudinal slot of the extending leg of the guide. The rings may be clamped against movement after adjustment of the sleeves.

8 Claims, 2 Drawing Sheets

ADJUSTABLE DRILL GUIDE

BACKGROUND OF THE INVENTION

This invention relates to drill guides as used in orthopaedic surgery and has specific relevance to an adjustable drill guide.

Heretofore, drill guides for use in orthopaedics include a plurality of holes for accommodating a drill bit therethrough. The drill guide may be connected to a prosthetic implant to aid the surgeon in aligning the drill bit with preformed holes in the implant. A fastening device such as a screw is inserted into the hole in the bone formed by the drill and seats within the implant. Typically, such drill guides include a body having a plurality of guide holes wherein the guide holes are fixed relative to the body. This requires that exact tolerances be maintained during manufacture of the drill guide so that a bore drilled using the guide matches a corresponding hole in the implant. If the drill guide is slightly mismatched to the implant, the bores through the bone will not exactly align with the holes in the implant.

In U.S. Pat. No. 4,865,025, a drill guide apparatus 1 is disclosed having a slider 4 that is moveable within channel 8 of branch 3b. Slider 4 includes two transverse passages 5 for receiving a drilling guide 6, which is dimensioned to receive a piercing pit 7 adaptable to a surgical drill. Slider 4 moves axially within passage 8 and is clamped into position by a locking mechanism. Although axial adjustment is possible, the apparatus requires that the holes in the bone or implant (t1 and t2) properly align with passages 5 of slider 4 upon a certain axial position of slider 4 within passage 8 and proper angular alignment of branch 3b within the bone or implant.

U.S Pat. No. 4,667,664, discloses a drill guide having a so-called target mechanism 46 for permitting alignment of the openings in the intramedullary nail. After the desired position is reached, set screw 70 is tightened for locking targeting mechanism in position. The target mechanism includes an alignment member with an axis that, through movement in four degrees of freedom, can be aligned coaxially with the blind hole. Again, however, any such adjustment is dependent upon the holes in the bone or implant properly aligning with passages within target mechanism 46.

SUMMARY OF THE INVENTION

The drill guide of this invention eliminates the problems discussed above by providing a drill guide wherein the guide holes are adjustable relative to the body to permit prealignment of the individual guides with the implant holes prior to drilling. After adjustment, the guides are fixed in place.

Accordingly, an object of the invention is to provide for a novel adjustable drill guide for a prosthetic implant.

Still another object of the invention is to provide for a drill guide for a prosthetic implant having adjustable guide holes to accommodate small misalignment between the holes in the implant and the individual guide holes.

The invention, in one form thereof, provides a guide for drilling into a patient's bone in alignment with an opening in a prosthetic implant. The drill guide includes a body adapted for connection to the prosthetic implant, and a leg extends from the body along the implant. A guide is carried by the leg for accommodating a drill bit therethrough. An adjustment device is carried by the leg in operative association with the guide member for shiftable movement of the guide member relative to the leg, thereby permitting alignment of the guide with the opening prior to drilling.

The present invention provides, in one form thereof, a guide for drilling into a patient's bone in alignment with an opening in a prosthetic implant. The drill guide includes a body that is connected to the implant and a leg extending from the body along the implant. The leg includes a plurality of axially spaced openings therein. A sleeve member, which accommodates a drill bit therethrough, is adjustably secured in each of the openings. Each of the sleeve members is independently adjustable within its respective opening for movement relative to the leg.

DESCRIPTION OF THE PREFERRED EMBODIMENT

The preferred embodiment herein described is not intended to be exhaustive or to limit the invention to the precise forms disclosed. Rather, it has been chosen and described in order to best explain its principles so that others skilled in the art might utilize its teachings. Although the disclosed embodiment relates to a hip stem implant, the invention is applicable to other types of implants as well.

Figure 1:
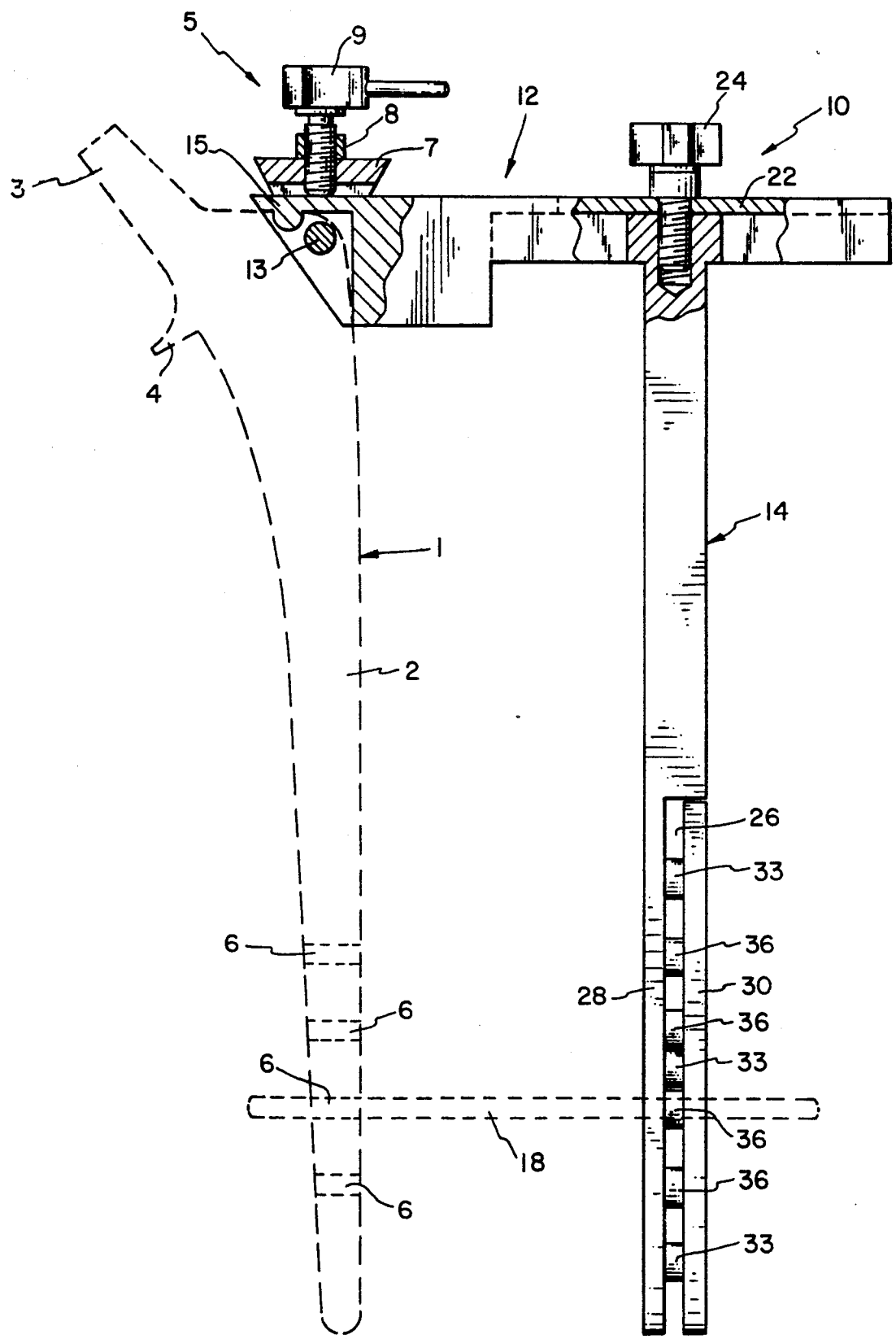
FIG. 1 is an elevational view of the adjustable drill guide of the invention connected to a prosthetic implant (shown in broken lines only). Portions of the drill guide are cut away for illustrative purposes.

Referring to FIG. 1 a prosthetic hip stem implant 1 is illustrated in broken lines and includes a stem 2 and neck 3 forming a collar 4 at their junction. A removal bore 5 is formed through the neck portion of implant 1. A plurality of throughbores 6 are formed through the distal tip of stem 2 to accommodate fastening devices (not shown) therethrough.

Figure 2:
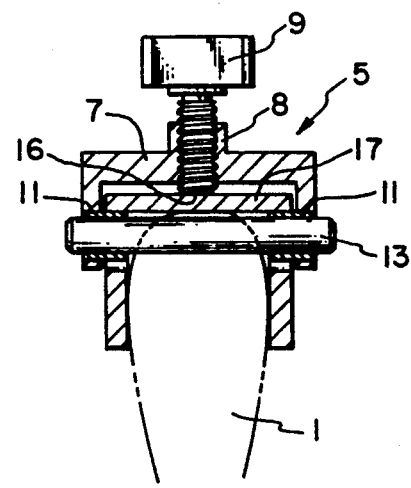
FIG. 2 is an enlarged, front view of the lock bias locating assembly of FIG. 1.

As illustrated in FIG. 1, drill guide 10 includes a body 12 adapted for connection to the implant 1 and a leg 14 extending downwardly from body 12. A lock bias locating assembly 5 is removably attachable to body 12 and includes a generally U-shaped attachment 7 including an internally threaded boss 8 for receiving threaded fastener 9. The downwardly extending legs of attachment 7 include pressed in tubes 11 for receiving a cross pin 13. In attaching assembly 5 to body 12 of drill guide 10, tubes 11 are aligned with corresponding openings (not shown) in tapered portion 15 of body 12. After aligning the openings in tapered portion 15 with the openings in implant 1, cross pin 13 is inserted therethrough as shown in FIG. 2. Fastener 9 is then threaded through boss 8 until the bottom surface 16 of fastener 9 engages top surface 17 of tapered portion 15. This pulls cross pin 13 and attachment 7 slightly upwardly to tightly secure implant 1 to body 12. As illustrated in FIG. 1, in use, body 12 removably engages the implant so as to maintain the body substantially perpendicular relative to the stem 2. A longitudinal slot 22 is formed in body 12.

Figure 3:
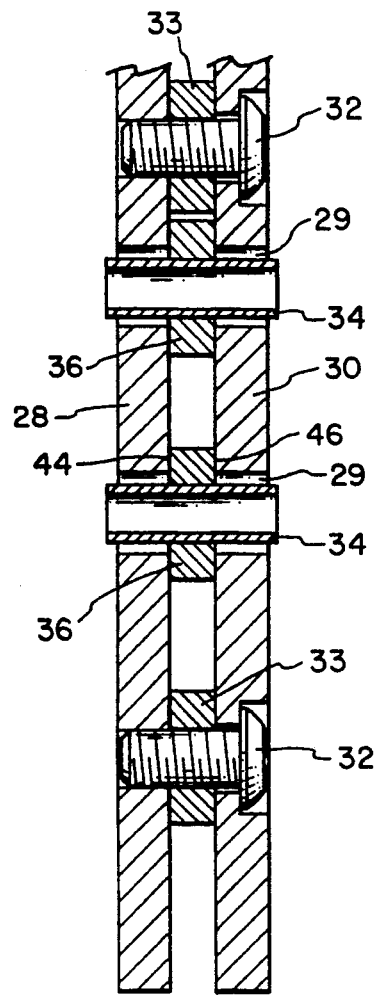
FIG. 3 is a cross-sectional view of the distal end of the drill guide of the invention.
Figure 4:
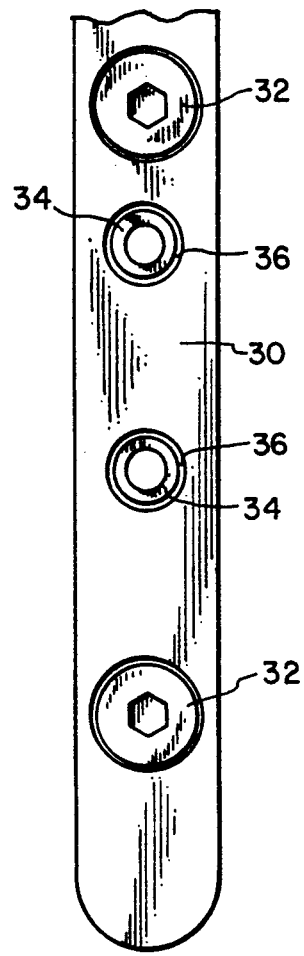
FIG. 4 is an elevational view of the distal end of the drill guide of the invention turned 90 degrees from FIG. 2.

Leg 14 is connected to body 12 by a fastener 24 traversing slot 22 and seating within the proximal end of leg 14 as shown. Leg 14 may be slid along the length of slot 22. The distal end of rod 14 includes a slot 26 forming tongues 28, 30. A plurality of screws 32 each extends through tongue 30 and a respective washer or retaining ring 33. Screws 32 seat with tongue 28 to draw tongues 28, 30 together. Tongues 28, 30 include a plurality of holes 29 therethrough (FIG. 3). A cylindrical sleeve 34 is positioned concentrically within each hole 29 of tongues 28 and 30 and is press fitted within a retaining ring 36. Retaining ring 36 is positioned between tongues 28, 30. It should be understood that each ring 36 and sleeve 34 are positioned in alignment with each hole 29 in tongues 28, 30.

In use, the drill guide 10 is initially connected to the implant 1, prior to seating of the implant, and fastener 24 is loosened to allow leg 14 to be slid in slot 22 toward the implant. Fastener 24 is then tightened to secure the leg against movement. Screws 32 are loosened which allows sleeves 34 and retaining rings 36 to axially shift within holes 29 between tongues 28 and 30. An alignment device such as a long probe 18 is inserted into each sleeve 34 and into the bores 6 of the implant to align each sleeve 34 with its corresponding bore. The sleeves 34 and retaining rings 36 move freely and independently with screws 32 loose. After all the sleeves have been aligned with the corresponding implant bore, screws 32 are tightened, which clamps retaining rings 36 between tongues 28, 30 in tight frictional engagement.

Drill guide 10 is removed and the implant is seated within a prepared canal of a bone. Once seated, fastener 24 is loosened and leg 14 is slid to the outermost position on body 12. Guide 10 is reattached to the implant which positions sleeves 34 in proper alignment with the bores 6 of the implant within the patient's bone. Once the guide is connected, a drill bit is inserted into each sleeve 34 and a bore is formed through the bone in alignment with each of the bores 6 of the implant.

Figure 5:
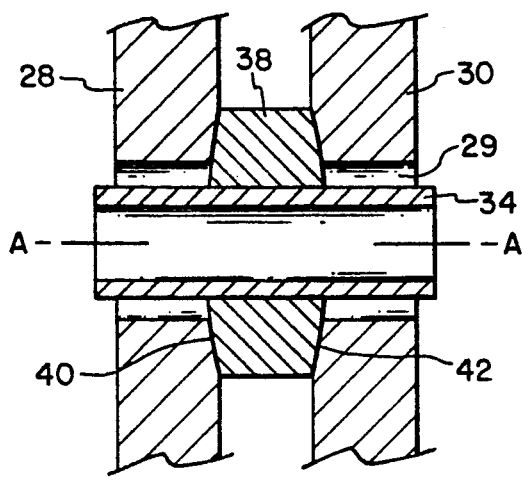
FIG. 5 is an enlarged, fragmentary view of an alternative embodiment to the drill guide shown in FIGS. 1–3.

An alternative embodiment of drill guide 10 is shown in FIG. 5, wherein a retaining ring 38 is shown that is different from retaining ring 36. Specifically, ring 38 includes generally arcuate surfaces 40 and 42, which engage arcuately shaped pockets in tongues 28 and 30, respectively. Ring 38 permits sleeve 34 to be aligned at an oblique angle with respect to central axis A—A of hole 29. In contrast, retaining ring 36 has flat surfaces 44 and 46 (FIG. 3), which permit only linear adjustment of sleeve 34 within hole 29. Ring 38 permits a slight angular adjustment of sleeve 34 within hole 29, if necessary to align sleeves 34 with corresponding bores 6 of the implant.

It should be understood that the adjustability of the sleeves provides a small correction factor at the time of surgery to align the guide sleeves with the bores in the implant.

It will be appreciated that the foregoing is presented by way of illustration only, and not by way of any limitation, and that various alternatives and modifications may be made to the illustrated embodiment without departing from the spirit and scope of the invention.

What is claimed is:

1. A guide for drilling into a patient's bone in alignment with an opening in a prosthetic implant, said drill guide including a body adapted for connection to said prosthetic implant, a leg extending from said body along said implant, guide means being carried by said leg for accommodating a drill bit therethrough,. and adjustment means carried by said leg in operative association with said guide means for shiftable movement of said guide means relative to said leg, thereby permitting alignment of said guide means with the opening prior to drilling, wherein said leg includes a longitudinal slot defining first and second distal leg portions, said guide means including a sleeve member carried by a ring member, said sleeve aligning with openings in said first and second digital leg portions.

2. The guide of claim 1, wherein said adjustment means includes a fastener device connecting said first and second distal leg portions for clamping engagement of said ring member therebetween to secure said sleeve against movement relative to said leg.

3. A guide for drilling into a patient's bone in alignment with an opening in a prosthetic implant, said drill guide comprising:
a body that is connectable to the implant;
a leg extending from said body along the implant;
a plurality of axially spaced openings in said leg; and
a sleeve member adjustable secured in each opening, each said sleeve member accommodating a drill bit therethrough, wherein each said sleeve member is independently adjustable within its respective opening for movement relative to said leg.

4. The guide of claim 3, wherein at least one of said sleeve members includes a central axis therethrough wherein said axis is angularly adjustable.

5. The guide of claim 3, wherein at least one of said sleeve members includes generally arcuate surfaces which permit said sleeve member to be aligned at an oblique angle with respect to a central axis extending through said opening.

6. A guide for drilling into a patient's bone in alignment with a plurality of openings in a prosthetic implant, said drill guide comprising:
a body that is connectable to the implant;
a leg extending from said body along the implant;
a plurality of axially spaced openings in said leg; and
a sleeve member adjustably secured in each opening, each said sleeve member accommodating a drill bit therethrough, wherein each said sleeve member is independently adjustable within its respective opening for movement relative to said leg;
wherein said leg includes a longitudinal slot defining first and second distal leg portions, wherein a fastener is provided for connecting said first and second distal leg portions for securing each said sleeve against movement relative to said leg.

7. A guide for drilling into a patient's bone in alignment with a plurality of openings in a prosthetic implant, said drill guide including a body adapted for connection to said prosthetic implant, a leg extending from said body along said implant, first guide means being carried by said leg for accommodating a drill bit therethrough, second guide means being carried by said leg for separately accommodating the drill bit therethrough and an adjustment means carried by said leg in operative association with each said guide means for shiftable movement of each said guide means relative to said leg, thereby permitting alignment of each said guide means with a respective opening prior to drilling, wherein said first guide means is shiftable independently of said second guide means.

8. The guide of claim 7 wherein said leg is slidable relative to said body.

* * * * *